(12) United States Patent
Bahl

(10) Patent No.: US 7,332,269 B2
(45) Date of Patent: *Feb. 19, 2008

(54) HCV CORE PROTEIN SEQUENCES

(75) Inventor: Chander Bahl, Flemington, NJ (US)

(73) Assignee: Ortho-Clinical Diagnostics, Inc., Rochester, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/268,569

(22) Filed: Oct. 10, 2002

(65) Prior Publication Data

US 2003/0152965 A1 Aug. 14, 2003

(51) Int. Cl.
*C12N 7/00* (2006.01)
*A61K 39/00* (2006.01)
*A61K 39/395* (2006.01)

(52) U.S. Cl. .................... 435/5; 424/130.1; 424/184.1; 435/339

(58) Field of Classification Search .................... 435/5; 436/518
See application file for complete search history.

(56) References Cited

U.S. PATENT DOCUMENTS

| 5,683,864 | A | * | 11/1997 | Houghton et al. | ............. | 435/5 |
| 5,712,087 | A | | 1/1998 | Houghton et al. | | |
| 6,346,375 | B1 | | 2/2002 | Chien | | |
| 6,630,298 | B2 | | 10/2003 | Chien et al. | | |
| 6,723,502 | B2 | | 4/2004 | Bahl et al. | | |
| 2003/0108563 | A1 | | 6/2003 | Bahl | | |
| 2003/0108858 | A1 | * | 6/2003 | Shah et al. | ............. | 435/5 |

FOREIGN PATENT DOCUMENTS

| DE | 4112743 C2 | 10/1992 |
| EP | 0967484 A1 | 12/1999 |
| EP | 1 020 727 | * 7/2000 |
| GB | 2051357 A | 1/1981 |

OTHER PUBLICATIONS

Honda, M. "Sequence analysis of putative structural regions of hepaptitis C virus isolated from 5 Japanese patients with hepatocellular carcinoma" Arch. Virol. 1993; 128: 163-169.*
Kumar, U. "Cloning and sequencing of the structural region and expression of putative core gene of hepatitis C virus from a British case of chronic sporadic hepatitis" J. Gen. Virol. 1992; 73: 1521-1525.*
Lee, S.R. et al.: "Efficacy Of A Hepatitis C Virus Core Antigen Enzyme-Linked Immunosorbent Assay For The Identification Of The 'Window-Phase' Blood Donation". Vox Sanguinis, 2001, 19-23, 80.
Tao, B. and Lee, K.C.: "Mutagenesis by PCR: PCR Technology: Current Innovations", CRC Press, Inc, 1994, Chapter 10.
Aoyagi et al., J Clin Micro 37(6):1802-1808 (1999).
Aoyagi et al., Clin Lab 47:119-127 (2001).
Barrera et al., Vox Sang 68:15-18 (1995).
Calcagno et al., AASLC Annual Meeting, Dallas, TX, USA, Nov. 10, 2001, Poster # 230.
Chien et al., J Clin Micro 37(5):1393-1397 (1999).
Courouce et al., Transfusion 40:1198-1202 (2000).
Icardi et al., J Clin Micro 39(9):3110-3114 (2001).
Masalova et al., J Med Virol 55:1-6 (1998).
Nakagiri et al., J Virol Methods 52:195-207 (1995).
Sallberg et al., J Med Virol 43:62-68 (1994).

* cited by examiner

*Primary Examiner*—Bruce R. Campell
*Assistant Examiner*—Agnieszka Boesen

(57) ABSTRACT

The present invention describes peptides and recombinant proteins containing Hepatitis C virus core protein sequence in which one or more of the amino acids have been modified or deleted to remove the ability of these proteins to bind to specific anti-HCV murine monoclonal antibodies. The deletions and modifications are designed as to maintain the ability of this protein to be used in immunoassays used for the detection of anti-HCV antibodies in individuals infected with HCV.

6 Claims, No Drawings

SEQUENCE LISTING

```
<160> NUMBER OF SEQ ID NOS: 19

<210> SEQ ID NO 1
<211> LENGTH: 15
<212> TYPE: PRT
<213> ORGANISM: Hepatitis C virus

<400> SEQUENCE: 1

Met Ser Thr Asn Pro Lys Pro Gln Lys Lys Asn Lys Arg Asn Thr
1               5                   10                  15

<210> SEQ ID NO 2
<211> LENGTH: 15
<212> TYPE: PRT
<213> ORGANISM: Hepatitis C virus

<400> SEQUENCE: 2

Lys Asn Lys Arg Asn Thr Asn Arg Arg Pro Gln Asp Val Lys Phe
```

```
                 1               5                  10                 15

<210> SEQ ID NO 3
<211> LENGTH: 15
<212> TYPE: PRT
<213> ORGANISM: Hepatitis C virus

<400> SEQUENCE: 3

Gln Asp Val Lys Phe Pro Gly Gly Gly Gln Ile Val Gly Gly Val
 1               5                  10                 15

<210> SEQ ID NO 4
<211> LENGTH: 15
<212> TYPE: PRT
<213> ORGANISM: Hepatitis C virus

<400> SEQUENCE: 4

Gln Ile Val Gly Gly Val Tyr Leu Leu Pro Arg Arg Gly Pro Arg
 1               5                  10                 15

<210> SEQ ID NO 5
<211> LENGTH: 15
<212> TYPE: PRT
<213> ORGANISM: Hepatitis C virus

<400> SEQUENCE: 5

Arg Arg Gly Pro Arg Leu Gly Val Arg Ala Thr Arg Lys Thr Ser
 1               5                  10                 15

<210> SEQ ID NO 6
<211> LENGTH: 15
<212> TYPE: PRT
<213> ORGANISM: Hepatitis C virus

<400> SEQUENCE: 6

Ala Thr Arg Lys Thr Ser Glu Arg Ser Gln Pro Arg Gly Arg Arg
 1               5                  10                 15

<210> SEQ ID NO 7
<211> LENGTH: 15
<212> TYPE: PRT
<213> ORGANISM: Hepatitis C virus

<400> SEQUENCE: 7

Pro Arg Gly Arg Arg Gln Pro Ile Pro Lys Ala Arg Arg Pro Glu
 1               5                  10                 15

<210> SEQ ID NO 8
<211> LENGTH: 15
<212> TYPE: PRT
<213> ORGANISM: Hepatitis C virus

<400> SEQUENCE: 8

Lys Ala Arg Arg Pro Glu Gly Arg Thr Trp Ala Gln Pro Gly Tyr
 1               5                  10                 15

<210> SEQ ID NO 9
<211> LENGTH: 15
<212> TYPE: PRT
<213> ORGANISM: Hepatitis C virus

<400> SEQUENCE: 9

Ala Gln Pro Gly Tyr Pro Trp Pro Leu Tyr Gly Asn Glu Gly Cys
 1               5                  10                 15
```

```
<210> SEQ ID NO 10
<211> LENGTH: 15
<212> TYPE: PRT
<213> ORGANISM: Hepatitis C virus

<400> SEQUENCE: 10

Tyr Gly Asn Glu Gly Cys Gly Trp Ala Gly Trp Leu Leu Ser Pro
1               5                   10                  15

<210> SEQ ID NO 11
<211> LENGTH: 15
<212> TYPE: PRT
<213> ORGANISM: Hepatitis C virus

<400> SEQUENCE: 11

Trp Leu Leu Ser Pro Arg Gly Ser Arg Pro Ser Trp Gly Pro Thr
1               5                   10                  15

<210> SEQ ID NO 12
<211> LENGTH: 15
<212> TYPE: PRT
<213> ORGANISM: Hepatitis C virus

<400> SEQUENCE: 12

Ser Trp Gly Pro Thr Asp Pro Arg Arg Arg Ser Arg Leu Asn Gly
1               5                   10                  15

<210> SEQ ID NO 13
<211> LENGTH: 15
<212> TYPE: PRT
<213> ORGANISM: Hepatitis C virus

<400> SEQUENCE: 13

Ser Arg Leu Asn Gly Lys Val Ile Asp Thr Leu Thr Cys Gly Phe
1               5                   10                  15

<210> SEQ ID NO 14
<211> LENGTH: 15
<212> TYPE: PRT
<213> ORGANISM: Hepatitis C virus

<400> SEQUENCE: 14

Leu Thr Cys Gly Phe Ala Asp Leu Met Gly Tyr Ile Pro Leu Val
1               5                   10                  15

<210> SEQ ID NO 15
<211> LENGTH: 15
<212> TYPE: PRT
<213> ORGANISM: Hepatitis C virus

<400> SEQUENCE: 15

Tyr Ile Pro Leu Val Gly Ala Pro Leu Gly Gly Ala Ala Arg Ala
1               5                   10                  15

<210> SEQ ID NO 16
<211> LENGTH: 15
<212> TYPE: PRT
<213> ORGANISM: Hepatitis C virus

<400> SEQUENCE: 16

Gly Ala Ala Arg Ala Leu Ala His Gly Val Arg Val Leu Glu Asp
1               5                   10                  15

<210> SEQ ID NO 17
```

-continued

```
<211> LENGTH: 15
<212> TYPE: PRT
<213> ORGANISM: Hepatitis C virus

<400> SEQUENCE: 17

Arg Val Leu Glu Asp Gly Val Asn Tyr Ala Thr Gly Asn Leu Pro
1               5                   10                  15

<210> SEQ ID NO 18
<211> LENGTH: 15
<212> TYPE: PRT
<213> ORGANISM: Hepatitis C virus

<400> SEQUENCE: 18

Thr Gly Asn Leu Pro Gly Cys Ser Phe Ser Ile Phe Leu Leu Ala
1               5                   10                  15

<210> SEQ ID NO 19
<211> LENGTH: 130
<212> TYPE: PRT
<213> ORGANISM: Hepatitis C virus

<400> SEQUENCE: 19

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
                20                  25                  30

Gly Val Tyr Leu Leu Pro Arg Arg Gly Pro Arg Leu Gly Val Arg Ala
                35                  40                  45

Thr Arg Lys Thr Ser Glu Arg Ser Gln Pro Arg Gly Arg Arg Gln Pro
    50                  55                  60

Ile Pro Lys Ala Arg Arg Pro Glu Gly Arg Ser Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Thr Asp Pro
                100                 105                 110

Arg Arg Arg Ser Arg Asn Leu Gly Lys Val Ile Asp Thr Leu Thr Cys
                115                 120                 125

Gly Phe
    130
```

HCV CORE PROTEIN SEQUENCES

BACKGROUND OF THE INVENTION

An estimated 170 million people worldwide have been infected by hepatitis C virus (HCV). In the next few years, the number of U.S. deaths for HCV-caused liver disease and cancer may overtake deaths caused by Acquired Immune Deficiency Syndrome (AIDS).

The transmission of HCV seems to require blood-to-blood contact. Carrying a single strand of ribonucleic acid (RNA), HCV contains just one gene, coding for a polyprotein that is subsequently cleaved into at least 10 functional proteins. Clearly, the ability to test the blood supply for HCV is of great importance. A sensitive assay that can detect infection at an early stage would be helpful.

HCV detection assays typically detect antibodies against HCV virus. These antibodies are detected in immunoassays using recombinant proteins and peptides containing HCV protein sequences. Most commercial anti-HCV assays use proteins from the following regions, core protein, NS3, NS4, and NS5 protein sequences.

Anti-HCV core antibodies are one of the most prevalent anti-HCV antibodies detected in chronic HCV infected individuals. HCV core protein contains multiple epitopes. Using synthetic peptides in the HCV core region, it has been shown that most of these epitopes are in the amino terminal end of this protein. For example, using overlapping peptides, each approximately 15 amino acids in length, an ELISA was developed to screen for anti-HCV antibodies in chronic HCV infected individuals. Table 1 below shows the peptide sequences. As shown in Table 2 below, HCV infected individuals have antibodies to two or more of these core peptides. Thus, it has been shown that the complete core peptide is not required to detect anti-core antibodies.

TABLE 1

| Peptide ID # | Amino Acid Sequence | HCV Polyprotein AA Location | |
|---|---|---|---|
| 0 | MSTNPKPQKKNKRNT | 1-15 | SEQ ID NO.:1 |
| 1 | KNKRNTNRRPQDVKF | 10-24 | SEQ ID NO.:2 |
| 2 | QDVKFPGGGQIVGGV | 20-34 | SEQ ID NO.:3 |
| 3 | QIVGGVYLLPRRGPR | 29-43 | SEQ ID NO.:4 |
| 4 | RRGPRLGVPATRKTS | 39-53 | SEQ ID NO.:5 |
| 5 | ATRKTSERSQPRGRR | 48-62 | SEQ ID NO.:6 |
| 6 | PRGRRQPIPKARRPE | 58-72 | SEQ ID NO.:7 |
| 7 | KARRPEGRTWAQPGY | 67-81 | SEQ ID NO.:8 |
| 8 | AQPGYPWPLYGNEGC | 77-91 | SEQ ID NO.:9 |
| 9 | YGNEGCGWAGWLLSP | 86-100 | SEQ ID NO.:10 |
| 10 | WLLSPRGSRPSWGPT | 96-110 | SEQ ID NO.:11 |
| 11 | SWGPTDPRRRSRLNG | 106-120 | SEQ ID NO.:12 |
| 12 | SRLNGKVIDTLTCGF | 116-130 | SEQ ID NO.:13 |
| 13 | LTCGFADLMGYIPLV | 126-140 | SEQ ID NO.:14 |
| 14 | YIPLVGAPLGGAARA | 136-150 | SEQ ID NO.:15 |
| 15 | GAARALAHGVRVLED | 146-160 | SEQ ID NO.:16 |
| 16 | RVLEDGVNYATGNLP | 156-170 | SEQ ID NO.:17 |
| 17 | TGNLPGCSFSIFLLA | 166-180 | SEQ ID NO.:18 |

TABLE 2

| Peptide | 0 | 1 | 2 | 3 | 4 | 5 | 6 | 7 | 8 | 9 | 10 | 11 | 12 | 13 | 14 | 15 | 16 | 17 |
|---|---|---|---|---|---|---|---|---|---|---|---|---|---|---|---|---|---|---|
| Neg | 0.044 | 0.004 | 0.021 | 0.075 | 0.059 | 0.069 | 0.076 | 0.103 | 0.020 | 0.034 | 0.002 | 0.088 | 0.051 | 0.028 | 0.023 | 0.034 | 0.041 | 0.042 |
| Neg | 0.045 | 0.065 | 0.017 | 0.081 | 0.051 | 0.081 | 0.103 | 0.111 | 0.033 | 0.035 | 0.002 | 0.085 | 0.038 | 0.030 | 0.023 | 0.030 | 0.038 | 0.052 |
| Neg | 0.050 | 0.003 | 0.014 | 0.075 | 0.087 | 0.079 | 0.094 | 0.102 | 0.025 | 0.034 | 0.002 | 0.071 | 0.038 | 0.033 | 0.021 | 0.031 | 0.039 | 0.047 |
| Neg | 0.014 | 0.043 | 0.134 | 0.023 | 0.034 | 0.039 | 0.034 | 0.039 | 0.012 | 0.018 | −0.001 | 0.025 | 0.009 | 0.009 | 0.008 | 0.013 | 0.010 | 0.020 |
| Neg | 0.015 | 0.039 | 0.119 | 0.021 | 0.033 | 0.030 | 0.030 | 0.034 | 0.013 | 0.019 | 0.000 | 0.026 | 0.011 | 0.010 | 0.005 | 0.012 | 0.010 | 0.016 |
| Neg | 0.013 | 0.036 | 0.126 | 0.027 | 0.053 | 0.032 | 0.037 | 0.042 | 0.013 | 0.016 | 0.001 | 0.037 | 0.013 | 0.009 | 0.009 | 0.012 | 0.009 | 0.017 |
| Neg | 0.016 | 0.004 | 0.104 | 0.020 | 0.039 | 0.034 | 0.003 | 0.041 | 0.019 | 0.019 | 0.000 | 0.041 | 0.011 | 0.017 | 0.006 | 0.010 | 0.008 | 0.021 |
| 9 | 0.256 | 2.500 | 2.500 | 0.425 | 1.443 | 0.016 | 0.218 | 0.248 | 0.062 | 0.015 | 0.025 | 0.049 | 0.030 | 0.013 | 0.012 | 0.021 | 0.012 | 0.028 |
| 11 | 0.413 | 2.500 | 2.500 | 0.917 | 0.229 | 0.647 | 0.114 | 0.262 | 0.166 | 0.159 | 0.002 | 0.055 | 0.022 | 0.027 | 0.021 | 0.042 | 0.247 | 0.088 |
| 15 | 0.044 | 0.661 | 2.500 | 0.067 | 0.577 | 0.057 | 0.110 | 0.072 | 0.061 | 0.032 | −0.003 | 0.045 | 0.018 | 0.031 | 0.020 | 0.039 | 0.035 | 0.080 |
| 18 | 1.643 | 0.887 | 2.500 | 0.641 | 0.100 | 0.052 | 0.032 | 0.576 | 0.037 | 0.022 | −0.001 | 0.040 | 0.006 | 0.010 | 0.009 | 0.025 | 0.036 | 0.039 |
| 20 | 0.021 | 0.111 | 2.500 | 2.500 | 0.482 | 0.032 | 0.029 | 0.045 | 0.028 | 0.015 | 0.011 | 0.035 | 0.009 | 0.014 | 0.009 | 0.017 | 0.019 | 0.059 |
| 21 | 2.500 | 2.500 | 2.500 | 2.262 | 2.500 | 0.516 | 2.259 | 0.080 | 0.378 | 0.018 | 0.022 | 0.064 | 0.013 | 0.024 | 0.017 | 0.024 | 0.135 | 0.035 |
| 27 | 0.032 | 2.500 | 2.500 | 0.089 | 2.500 | 1.652 | 1.349 | 0.043 | 0.039 | 0.034 | 0.033 | 0.026 | 0.012 | 0.018 | 0.013 | 0.028 | 0.287 | 0.008 |
| 30 | 2.500 | 2.500 | 2.500 | 2.500 | 0.183 | 0.044 | 0.075 | 0.993 | 0.078 | 0.035 | 0.028 | 0.190 | 0.023 | 0.025 | 0.022 | 0.028 | 0.042 | 0.043 |
| 35 | 0.022 | 0.278 | 0.912 | 0.031 | 0.036 | 0.116 | 0.079 | 0.049 | 0.062 | 0.010 | 0.005 | 0.026 | 0.005 | 0.006 | 0.009 | 0.020 | 0.007 | 0.020 |
| 36 | 0.059 | 0.129 | 2.500 | 0.090 | 0.131 | 0.060 | 0.093 | 0.148 | 0.090 | 0.037 | 0.003 | 0.050 | 0.018 | 0.060 | 0.077 | 0.062 | 0.129 | 0.079 |
| 37 | 2.500 | 2.500 | 2.500 | 0.219 | 0.130 | 0.090 | 0.169 | 0.223 | 0.147 | 0.040 | 0.018 | 0.065 | 0.016 | 0.051 | 0.051 | 0.025 | 0.080 | 0.110 |
| 39 | 0.165 | 2.500 | 2.500 | 2.500 | 0.124 | 1.217 | 2.351 | 2.500 | 0.397 | 0.056 | 0.015 | 1.319 | 0.017 | 0.050 | 0.056 | 0.041 | 0.200 | 0.190 |
| 40 | 0.058 | 2.500 | 2.500 | 2.500 | 0.098 | 0.066 | 0.060 | 0.755 | 0.093 | 0.024 | 0.000 | 0.059 | 0.013 | 0.028 | 0.017 | 0.032 | 0.068 | 0.101 |
| 42 | 0.022 | 0.043 | 2.500 | 0.031 | 0.023 | 0.150 | 0.018 | 0.036 | 0.023 | 0.011 | −0.001 | 0.032 | 0.005 | 0.014 | 0.006 | 0.010 | 0.012 | 0.031 |
| 43 | 0.158 | 0.612 | 0.368 | 0.033 | 0.065 | 0.103 | 0.069 | 0.075 | 0.053 | 0.051 | 0.001 | 0.055 | 0.025 | 0.022 | 0.015 | 0.023 | 0.029 | 0.035 |
| 44 | 0.042 | 2.240 | 2.500 | 0.511 | 0.070 | 0.060 | 0.086 | 0.301 | 0.108 | 0.066 | −0.002 | 0.143 | 0.028 | 0.041 | 0.028 | 0.047 | 0.061 | 0.076 |
| 45 | 1.002 | 2.500 | 2.500 | 0.174 | 0.713 | 0.055 | 0.129 | 1.722 | 1.896 | 0.029 | −0.003 | 0.069 | 0.038 | 0.038 | 0.055 | 0.022 | 0.136 | 0.039 |

TABLE 2-continued

| Peptide | 0 | 1 | 2 | 3 | 4 | 5 | 6 | 7 | 8 | 9 | 10 | 11 | 12 | 13 | 14 | 15 | 16 | 17 |
|---|---|---|---|---|---|---|---|---|---|---|---|---|---|---|---|---|---|---|
| 46 | 0.016 | 0.031 | 2.500 | 0.022 | 0.021 | 0.021 | 0.038 | 0.035 | 0.031 | 0.027 | −0.002 | 0.027 | 0.016 | 0.015 | 0.013 | 0.026 | 0.019 | 0.037 |
| 47 | 2.484 | 2.500 | 2.500 | 0.449 | 0.750 | 0.593 | 0.102 | 2.006 | 0.331 | 0.017 | −0.004 | 0.034 | 0.012 | 0.014 | 0.007 | 0.026 | 0.014 | 0.032 |
| 48 | 0.427 | 0.201 | 2.500 | 0.364 | 0.356 | 0.038 | 0.049 | 0.070 | 0.027 | 0.029 | −0.001 | 0.040 | 0.018 | 0.011 | 0.013 | 0.025 | 0.014 | 0.095 |
| 49 | 0.019 | 0.483 | 2.500 | 0.044 | 0.045 | 0.047 | 0.050 | 0.246 | 0.039 | 0.025 | −0.005 | 0.033 | 0.019 | 0.014 | 0.013 | 0.030 | 0.016 | 0.085 |
| 50 | 0.668 | 2.500 | 2.500 | 0.568 | 1.233 | 0.277 | 0.154 | 2.500 | 0.882 | 0.024 | −0.001 | 0.035 | 0.014 | 0.012 | 0.007 | 0.017 | 0.044 | 0.055 |
| 52 | 2.500 | 2.500 | 2.500 | 0.948 | 1.116 | 1.619 | 0.026 | 0.267 | 0.112 | 0.019 | 0.026 | 0.042 | 0.012 | 0.007 | 0.009 | 0.019 | 0.008 | 0.044 |
| 53 | 0.823 | 2.500 | 2.500 | 0.428 | 2.500 | 0.780 | 0.086 | 2.500 | 1.566 | 0.025 | 0.001 | 0.050 | 0.014 | 0.020 | 0.011 | 0.022 | 0.019 | 0.028 |
| 54 | 1.577 | 2.500 | 2.500 | 2.500 | 2.500 | 2.500 | 2.500 | 2.500 | 2.500 | 0.020 | 0.032 | 0.053 | 0.021 | 0.012 | 0.012 | 0.020 | 0.017 | 0.038 |
| 55 | 0.017 | 0.083 | 2.500 | 0.047 | 0.018 | 0.023 | 0.071 | 0.042 | 0.019 | 0.017 | −0.002 | 0.026 | 0.015 | 0.015 | 0.012 | 0.026 | 0.014 | 0.030 |
| 58 | 2.500 | 2.500 | 2.500 | 2.283 | 2.500 | 2.500 | 2.500 | 2.500 | 0.810 | 0.037 | 0.073 | 0.067 | 0.018 | 0.019 | 0.021 | 0.025 | 0.159 | 0.059 |
| 59 | 0.015 | 1.805 | 2.500 | 0.023 | 2.500 | 0.019 | 0.180 | 0.038 | 0.070 | 0.039 | 0.027 | 0.017 | 0.012 | 0.015 | 0.018 | 0.015 | 0.023 | 0.049 |
| 60 | 0.053 | 2.500 | 2.500 | 0.255 | 2.500 | 0.102 | 1.266 | 0.666 | 2.500 | 0.034 | −0.003 | 0.153 | 0.026 | 0.019 | 0.022 | 0.039 | 0.097 | 0.063 |
| 62 | 0.018 | 0.053 | 2.500 | 1.178 | 0.025 | 0.031 | 0.041 | 0.060 | 0.028 | 0.017 | −0.002 | 0.039 | 0.013 | 0.012 | 0.010 | 0.017 | 0.010 | 0.048 |
| 63 | 0.009 | 0.016 | 0.027 | 0.012 | 0.017 | 0.013 | 1.225 | 0.028 | 0.012 | 0.017 | −0.004 | 0.026 | 0.007 | 0.007 | 0.006 | 0.010 | 0.057 | 0.020 |
| 65 | 1.440 | 0.041 | 0.026 | 0.040 | 0.032 | 0.056 | 0.052 | 0.062 | 0.020 | 0.040 | 0.023 | 0.051 | 0.018 | 0.023 | 0.023 | 0.019 | 0.020 | 0.035 |
| 66 | 2.060 | 2.500 | 2.500 | 1.030 | 2.500 | 0.508 | 0.144 | 2.500 | 2.500 | 0.013 | 0.009 | 0.060 | 0.007 | 0.009 | 0.009 | 0.014 | 0.025 | 0.018 |
| 67 | 2.500 | 2.500 | 2.500 | 2.500 | 2.500 | 1.338 | 0.406 | 2.500 | 0.135 | 0.031 | 0.003 | 0.091 | 0.021 | 0.027 | 0.028 | 0.032 | 0.042 | 0.077 |
| 68 | 2.500 | 2.500 | 2.500 | 1.105 | 0.415 | 0.358 | 1.025 | 2.500 | 0.263 | 0.028 | 0.006 | 0.039 | 0.023 | 0.025 | 0.022 | 0.024 | 0.034 | 0.037 |
| 70 | 0.745 | 2.500 | 2.500 | 0.342 | 2.500 | 0.200 | 0.049 | 0.075 | 1.730 | 0.030 | 0.009 | 0.119 | 0.015 | 0.025 | 0.022 | 0.027 | 0.056 | 0.050 |
| 73 | 0.031 | 2.392 | 2.500 | 0.049 | 0.629 | 0.935 | 0.596 | 1.119 | 0.081 | 0.040 | 0.009 | 0.052 | 0.028 | 0.036 | 0.031 | 0.038 | 0.043 | 0.059 |
| 75 | 0.037 | 2.500 | 2.500 | 1.435 | 1.342 | 0.107 | 0.287 | 0.094 | 0.080 | 0.049 | 0.012 | 0.031 | 0.013 | 0.030 | 0.017 | 0.021 | 0.058 | 0.050 |
| 78 | 2.500 | 2.500 | 2.500 | 0.269 | 2.500 | 0.298 | 0.051 | 2.500 | 0.040 | 0.057 | 0.006 | 0.084 | 0.013 | 0.022 | 0.014 | 0.021 | 0.022 | 0.030 |
| 80 | 0.280 | 2.500 | 2.500 | 0.674 | 0.318 | 0.972 | 0.048 | 2.118 | 0.040 | 0.021 | 0.022 | 0.024 | 0.015 | 0.010 | 0.008 | 0.014 | 0.066 | 0.031 |
| 84 | 0.012 | 0.075 | 2.500 | 0.025 | 0.190 | 0.145 | 0.106 | 0.099 | 0.019 | 0.028 | 0.050 | 0.018 | 0.009 | 0.010 | 0.009 | 0.013 | 0.009 | 0.026 |
| 90 | 0.019 | 0.306 | 2.500 | 0.039 | 2.500 | 0.689 | 0.033 | 0.301 | 0.195 | 0.021 | 0.005 | 0.033 | 0.011 | 0.017 | 0.010 | 0.013 | 0.014 | 0.018 |

A recent report indicates that the HCV core protein can be detected in HCV infected individuals before the appearance of anti-HCV antibodies. (S. Lee et al., Vox Sanguinis, 2001; 80: 19-23). Therefore, we suggest that a more efficient way of early detection of HCV infection would be a combination assay able to detect HCV core protein and anti-HCV antibodies including anti-core antibodies.

SUMMARY OF THE INVENTION

The present invention describes peptides and recombinant proteins containing Hepatitis C virus core protein sequence in which one or more of the amino acids have been modified or deleted to remove the ability of these proteins to bind to specific anti-HCV murine monoclonal antibodies. These modifications were made in the in the underlined regions shown in Table 3 below. The deletions and modifications are designed as to maintain the ability of this protein to be used in immunoassays used for the detection of anti-HCV antibodies in individuals infected with HCV. These modified core proteins can be used in a combination assay for the simultaneous detection of HCV core protein and anti-HCV antibodies. The combination assay will be able to detect HCV assay earlier than the currently used antibody assays.

DETAILED DESCRIPTION OF THE INVENTION

One object of the invention is to develop peptide sequences that can detect anti-HCV antibodies in the presence of anti-core monoclonal antibodies to detect HCV core antigen. One use therefore of these modified core antigens will be to use them in an anti-HCV/HCV core assay, or "combination assay".

For this purpose, two or more monoclonal antibodies from Table 4 can be co-coated with one or more modified HCV core proteins on a solid phase thereby enabling the solid phase to capture anti-HCV core antibodies and core antigen. The modification is accomplished by removing the epitope for the antibody being used for detection or capture of HCV core. The removal of epitopes can be achieved by means known in the art such as deleting parts of the core sequence or altering amino acids in the epitope sequence. This can be achieved, for example, by synthesizing these peptides by chemical synthesis using commercially available peptide synthesizers or by modifying recombinant clones expressing HCV core protein. The recombinant sequences can be modified by primer dependent single or multiple site mutagenesis or primer dependent deletions. (B. Tao and K. C. Lee, PCR Technology Current Innovations, 1994 by CRC Press, Inc., Chapter 10, Mutagenesis by PCR).

Another object of the invention is to identify immunodominant regions of HCV core protein.

Another object of the present invention is to determine the pattern of reactivity to core peptides among HCV infected individuals presenting anti-core antibodies.

The peptides of the invention were generated by maintaining the highly reactive portions of the core protein and making modifications to the remaining parts of the sequence such that the peptide would not be detected by an antibody used to detect core protein in an assay.

In a preferred embodiment, the peptide would be modified by either substitution of amino acids or deletion of amino acids in the regions underlined in Table 3. The remainder of the sequence shown in Table 3 should not be altered.

In another preferred embodiment the peptides would be used in a combination assay. That is one that is capable of detecting both HCV antigens and antibodies simultaneously.

TABLE 3

HCV core protein sequence:

SEQ ID NO.:19
MSTNPKPQRKTKRNTNRRPQDVKFPGGGQIVGGVYLLPRRGPRLGVPATR

KTSERSQPRGRRQPIPKARRPEGRSWAQPGYPWPLYGNEGCGWAGWLLSP

RGSRPSWGPTDPRRRSRNLGKVIDTLTCGF

The effectiveness and advantages of the invention are further illustrated by the following examples.

EXAMPLE 1

Synthetic Peptides

Synthetic peptides covering the entire sequence of HCV core protein sequence were used. Eighteen overlapping peptides shown in Table 1 were chemically synthesized by solid phase peptide synthesis using a peptide synthesizer. All of the peptides were synthesized with a C-terminal cysteine amide residue. Peptides were cleaved form the resin and purified by reverse phase liquid chromatography. Purity of each of these peptides, based on reverse phase HPLC analysis was greater that ninety-five (95%). The sequence of each peptide was confirmed by amino acid analysis of the acid hydrolysate of the peptide. The structural identities of the peptides were confirmed mass spectrometry. All of the peptides had the molecular weight expected.

EXAMPLE 2

Synthetic peptides were coated onto Immulon 2 microwells (made by Dyanatech) in 50 mM borate buffer at a concentration of 1 ug/ml. To each microwell, 200 ul of peptide solution was added and the microwells were incubated at 25 degrees Celsius for 16-20 hours. The microwells were aspirated and washed once with phosphate buffer saline (PBS) containing TWEEN 20 to remove any unbound peptide. The microwells were then post coated with 300 ul of PBS containing one percent (1%) bovine serum albumin (BSA) and three percent (3%) sucrose to block all of the available protein binding sites. After 2-4 hours, the plates were aspirated, turbo dried and stored in sealed pouches at 2-8 degrees Celsius.

EXAMPLE 3

Synthetic Peptide ELISA

The sample, 10 ul in 200 ul of diluent, suspected of being infected with HCV was added into the peptide coated microwell. After incubation for approximately one hour the microwells were washed. To the washed microwells anti-human IgG were labeled with horse radish peroxidase was added. After an incubation for thirty minutes the microwells were washed and a solution of ORTHO phenylenedaamine buffer and hydrogen peroxide added to each well. After approximately 30 minutes sulfuric acid were added to each well to stop the reaction. An orange or yellow color indicated the presence of anti-HCV antibodies in the sample.

Table 4

Monoclonal Antibodies

The table below identifies 15 antibodies. The antibodies were screened at every stage of antibody development with microtitrewell plates coated with immunogen. The immunogen used to immunize the mice that produced each strain of monoclonal antibody is identified as one of the following: peptide ODS 243, a large peptide further defined in Example 1; "FLC" means full length core antigen, defined in Example 1; or KLH conjugated core peptide #8, a short peptide, further defined herein. The specificity of each to a numbered peptide is shown and the amino acid sequences of each numbered peptide is identified herein. Furthermore, the epitope to which the antibody specifically binds is included in the last column, defined by the amino acids that encode for the epitope.

| ATCC # | AG-FUSION #, clone | IMMUNOGEN | ISOTYPE | SPECIFICITY | AA |
| --- | --- | --- | --- | --- | --- |
| PTA-3811 | ODS243, 7B4F11 | Peptide ODS 243 | IgG 2b | HCV core peptide #8 | 77-91 |
| PTA-3803 | ODS243, 1E3D12 | Peptide ODS 243 | IgG2a | HCV core peptide #9 | 86-100 |
| PTA-3802 | ODS243, 7C12C4 | Peptide ODS 243 | IgG2b | HCV core peptide #8 | 77-91 |
| PTA-3813 | core#3, 2A11C6 | FLC | IgG1 | HCV core peptide# 11 | 106-120 |
| PTA-3809 | Core#12, 1B7A1 | FLC | IgG1 | HCV core peptide# 3 | 29-43 |
| PTA-3805 | CORE#13, 5A12G12 | FLC | IgG1 | HCV core peptide# 4 | 39-53 |
| PTA-3812 | Core#13, 4H7E7 | FLC | IgG1 | HCV core peptide# 5 | 48-62 |
| PTA-3806 | Core#13, 12F4A11 | FLC | IgG1 | HCV core peptide# 6 | 58-72 |
| PTA-3804 | Core#13, 14D12A12 | FLC | IgG1 | HCV core peptide# 7 | 67-81 |
| PTA-3807 | c22-8#4, 6D8E8 | KLH Conjugated core peptide #8 | IgG1 | HCV core peptide# 8 | 77-91 |
| PTA-3800 | Core#12, 4G10G6 | FLC | IgG2b | HCV core peptide# 10 | 96-110 |
| PTA-3801 | Core#13, 6E7E1 | FLC | IgG2a | HCV core peptide# 11 | 106-120 |
| PTA-3810 | Core#13, 11D12A6 | FLC | IgG2b | HCV core peptide# 11 | 106-120 |
| PTA-3808 | Core#13, 14B7C3 | FLC | IgG3 | HCV core peptide# 11 | 106-120 |

-continued

| ATCC # | AG-FUSION #, clone | IMMUNOGEN | ISOTYPE | SPECIFICITY | AA |
|---|---|---|---|---|---|
| PTA-3799 | Core#12, 4A6H3 | FLC | IgG1 | HCV core peptide# 16 | 156-170 |

EXAMPLE 4

Use of Modified Core Peptides in an Anti-HCV ELISA

A peptide consisting of HCV core immunodominant region amino acids 1-43 was chemically synthesized. Another peptide with certain deletions in this region, namely, amino acids 1-8 and 31-33 were deleted, was also synthesized. These peptides were used to test 40 chronic HCV patients' serum samples for anti-HCV antibody status. The results indicated that 39 of the 40 patients were not affected by deletion of these sequences. The deletion peptides can be used in combination with anti-HCV monoclonal antibodies, such as the ones shown in Table 4, in a combination assay. Peptides with deletions of amino acids 31-33 can be used with any of the monoclonal antibodies shown in Table 4.

TABLE 5

| Peptide/Specimen ID | 265-2 | 266-2 | 271-2 | 272-2 |
|---|---|---|---|---|
| 11 | 2.500 | 2.500 | 2.500 | 2.500 |
| 15 | 2.500 | 2.500 | 2.500 | 2.500 |
| 18 | 2.500 | 2.500 | 2.500 | 2.500 |
| 20 | 2.500 | 2.500 | 2.500 | 2.500 |
| 21 | 2.500 | 2.500 | 2.500 | 2.500 |
| 27 | 2.500 | 2.500 | 2.500 | 2.500 |
| 30 | 2.500 | 2.500 | 2.500 | 2.500 |
| 35 | 0.762 | 0.911 | 0.507 | 0.611 |
| 36 | 2.500 | 2.500 | 2.500 | 2.500 |
| 37 | 2.500 | 2.500 | 2.500 | 2.500 |
| 39 | 2.500 | 2.500 | 2.500 | 2.500 |
| 40 | 2.500 | 2.500 | 2.500 | 2.500 |
| 42 | 2.500 | 2.500 | 2.500 | 2.500 |
| 43 | 1.621 | 1.255 | 1.382 | 1.443 |
| 44 | 2.500 | 2.500 | 2.500 | 2.500 |
| 45 | 2.500 | 2.500 | 2.500 | 2.500 |

TABLE 5-continued

| Peptide/Specimen ID | 265-2 | 266-2 | 271-2 | 272-2 |
|---|---|---|---|---|
| 46 | 2.003 | 1.863 | 1.058 | 1.829 |
| 47 | 2.500 | 2.500 | 2.500 | 2.500 |
| 48 | 2.500 | 2.500 | 2.500 | 2.500 |
| 49 | 2.500 | 2.500 | 2.500 | 2.500 |
| 50 | 2.500 | 2.500 | 2.500 | 2.500 |
| 52 | 2.500 | 2.500 | 2.500 | 2.500 |
| 53 | 2.500 | 2.500 | 2.500 | 2.500 |
| 54 | 2.500 | 2.500 | 2.500 | 2.500 |
| 55 | 2.500 | 2.500 | 2.500 | 2.500 |
| 58 | 2.500 | 2.500 | 2.500 | 2.500 |
| 59 | 2.500 | 2.500 | 2.500 | 2.500 |
| 60 | 2.500 | 2.500 | 2.500 | 2.500 |
| 62 | 2.500 | 2.500 | 2.500 | 2.500 |
| 65 | 0.056 | 0.045 | 2.237 | 1.704 |
| 66 | 2.500 | 2.500 | 2.500 | 2.500 |
| 67 | 2.500 | 2.500 | 2.500 | 2.500 |
| 68 | 2.500 | 2.500 | 2.500 | 2.500 |
| 70 | 2.500 | 2.500 | 2.500 | 2.500 |
| 73 | 2.500 | 2.500 | 2.500 | 2.500 |
| 75 | 2.500 | 2.500 | 2.500 | 2.500 |
| 78 | 2.500 | 2.500 | 2.500 | 2.500 |
| 80 | 2.500 | 2.500 | 2.500 | 2.500 |
| 84 | 2.500 | 2.500 | 2.170 | 2.500 |
| 90 | 2.500 | 2.500 | 2.500 | 2.500 |

Peptide 265 HCV Polyprotein Amino Acid Sequence 10-43
Peptide 266 HCV Polyprotein Amino Acid Sequence 8-43
Peptide 271 HCV polyprotein Amino Acid Sequence 1-43 with AA 31, 32 and 33 deleted
Peptide 272 HCV Polyprotein Amino Acid Sequence 1-43 Consensus sequence

I claim:

1. A kit for the simultaneous detection of HCV antibody and HCV antigen comprising A) a solid phase coated with
    1) an HCV core peptide, comprising the amino acid sequence of SEQ ID NO: 19, wherein at least two of the following amino acid segments have one or more amino acids deleted or one or more amino acids altered,
        i) MSTNPKPQRK (residues 1-10);
        ii) IVGGVYLL (residues 30-37);

iii) RLGVRATR (residues 43-50); and iv) AQPGYPWPLYGNEGCGWAGWLLSPRG-SRPSWGPTDPRRRSRNLGKV IDTLTCGF (residues 77-130);

2) HCV non-core protein, and 3) at least one anti-HCV monoclonal antibody that binds to HCV core antigen and does not bind with the HCV core peptide described in A) 1); and B) a labeled anti-HCV monoclonal antibody that binds to HCV core antigen and does not bind to the HCV core peptide described in A) 1) and does not bind to the same epitope as the anti-HCV monoclonal antibody described in A) 3).

2. The kit according to claim 1 wherein the HCV non-core protein is selected from c200 and NS5.

3. The kit according to claim 1 wherein the labeled anti-HCV monoclonal antibody is labeled with an enzyme, a fluorophore, or a radioactive label.

4. The kit according to claim 1 wherein the solid phase is a microtitre well, polystyrene bead, magnetic bead or membrane.

5. An isolated HCV core peptide, comprising the amino acid sequence of SEQ ID NO: 19, wherein at least two of the following segments of amino acids have one or more amino acids deleted or one or more amino acids altered,
  i) MSTNPKPQRK (residues 1-10);
  ii) IVGGVYLL (residues 30-37);
  iii) RLGVRATR (residues 43-50); and
  iv) AQPGYPWPLYGNEGCGWAGWLLSPRG-SRPSWGPTDPRRRSRNLGKV IDTLTCGF (residues 77-130), and wherein amino acids 11-29, 38-42, and 51-76 are not deleted or altered.

6. The isolated HCV core peptide claimed in claim 5 wherein amino acids MSTNPKPQ have been deleted from section i) and amino acids VGG have been deleted from section ii).

* * * * *